US012714374B2

(12) United States Patent
Su et al.

(10) Patent No.: US 12,714,374 B2
(45) Date of Patent: Aug. 25, 2026

(54) NORMALIZATION CORRECTION METHOD AND APPARATUS FOR PET SYSTEM, AND DEVICE AND READABLE STORAGE MEDIUM

(71) Applicant: Sino Canada Health Engineering Research Institute (Hefei) Ltd., Hefei (CN)

(72) Inventors: Jin Su, Hefei (CN); Gong Zhang, Hefei (CN); Huabin Wang, Hefei (CN)

(73) Assignee: Sino Canada Health Engineering Research Institute (Hefei) Ltd., Hefei (CN)

( * ) Notice: Subject to any disclaimer, the term of this patent is extended or adjusted under 35 U.S.C. 154(b) by 245 days.

(21) Appl. No.: 18/568,389

(22) PCT Filed: Jun. 8, 2021

(86) PCT No.: PCT/CN2021/098956
§ 371 (c)(1),
(2) Date: Dec. 8, 2023

(87) PCT Pub. No.: WO2022/257015
PCT Pub. Date: Dec. 15, 2022

(65) Prior Publication Data

US 2024/0268772 A1 Aug. 15, 2024

(51) Int. Cl.
*A61B 6/03* (2006.01)
*A61B 6/42* (2024.01)
*A61B 6/58* (2024.01)

(52) U.S. Cl.
CPC ............ *A61B 6/037* (2013.01); *A61B 6/4208* (2013.01); *A61B 6/583* (2013.01)

(58) Field of Classification Search
CPC ....... A61B 6/037; A61B 6/4208; A61B 6/583; G06T 11/00
See application file for complete search history.

(56) References Cited

U.S. PATENT DOCUMENTS

2010/0272335 A1* 10/2010 Hu ........................ G06T 11/006 711/E12.001

FOREIGN PATENT DOCUMENTS

CN 104751499 A 7/2015
CN 105556342 A 5/2016
(Continued)

OTHER PUBLICATIONS

"International Application Serial No. PCT/CN2021/098956, International Search Report dated Mar. 4, 2022", w/ English Translation, (Mar. 4, 2022), 7 pgs.
(Continued)

*Primary Examiner* — Jianxun Yang
(74) *Attorney, Agent, or Firm* — Schwegman Lundberg & Woessner, P.A.

(57) ABSTRACT

Provided is a normalization correction method for a PET system a detector including crystals. The method includes: obtaining a coincidence event dataset including a plurality of lines of response; calculating a geometric symmetry value of each line of response; grouping the plurality of lines of response according to the geometric symmetry value, where a plurality of lines of response in a group have a same geometric symmetry value; calculating a number of coincidence events of a same group through accumulation; cyclically calculating, according to the calculated number of the coincidence events for the same group, a geometric factor value of each group, where each line of response in the same group of lines of response has a same geometric factor value; cyclically calculating crystal efficiency factor values of the crystals; and calculating normalization factor values of the lines of response respectively, according to the geometric factor value and the crystal efficiency factor values.

18 Claims, 6 Drawing Sheets

(56) References Cited

FOREIGN PATENT DOCUMENTS

| | | | | |
|---|---|---|---|---|
| CN | 108209958 A | | 6/2018 | |
| CN | 109965897 A | | 7/2019 | |
| WO | WO-2015006123 A1 | | 1/2015 | |
| WO | WO-2015022606 A1 | * | 2/2015 | ........... G01T 1/2985 |

OTHER PUBLICATIONS

"International Application Serial No. PCT/CN2021/098956, Written Opinion dated Mar. 4, 2022", (Mar. 4, 2022), 4 pgs.

"Chinese Application No. 202180099138.X, Office Action dated Mar. 21, 2026", w English Translation, 03 21 2026, 12 pgs.

* cited by examiner

NORMALIZATION CORRECTION METHOD AND APPARATUS FOR PET SYSTEM, AND DEVICE AND READABLE STORAGE MEDIUM

PRIORITY APPLICATIONS

This application is a U.S. National Stage Filing under 35 U.S.C. § 371 from International Application No. PCT/CN2021/098956, filed on Jun. 8, 2021, and published as WO2022/257015 on Dec. 15, 2022; the benefit of priority of which is hereby claimed herein, and which application and publication is hereby incorporated herein by reference in its entirety.

TECHNICAL FIELD

The present disclosure relates to fields of image processing technology and medical equipment technology, and in particular, to a normalization correction method and a normalization correction apparatus for a PET system, a device, and a readable storage medium.

BACKGROUND

In a PET (Positron Emission Tomography) system, a clinical imaging process specifically includes that a radioactive nuclide (such as F-18 etc.) which emits positrons is marked onto a compound that may participate in human tissue blood flow or metabolic process, and the radioactive nuclide of the compound marked with the positrons is injected into a body of the patient. A PET scanning is performed on the patient within an effective field of view (FOV) of the PET. The positrons emitted by the radioactive nuclide move about 1 mm in the body and combine with negatrons in the tissue to produce annihilation radiation, so as to generate two γ photons with equal energy (511 KeV) and opposite directions. By using a detection system of a PET apparatus, it is possible to detect the pair of γ photons, so as to analyze the presence of positrons and reconstruct a PET image that reflects a metabolism of various tissues of an organism, thereby acquiring a concentration distribution of a tracer in the organism being detected.

The above information disclosed in this section is only for the purpose of understanding the background of the technical concept of the present disclosure. Therefore, the above information may contain information that does not constitute the prior art.

SUMMARY

In an aspect, a normalization correction method for a PET system is provided, where the PET system includes a detector, the detector includes a plurality of crystals, and the normalization correction method includes:

- acquiring a coincidence event dataset, where the coincidence event dataset includes a plurality of lines of response;
- calculating a geometric symmetry value of each line of response;
- grouping the plurality of lines of response according to the geometric symmetry value of each line of response, where a plurality of lines of response in a group of lines of response have a same geometric symmetry value;
- calculating a number of coincidence events of a same group of lines of response through accumulation;

- cyclically calculating, according to the calculated number of the coincidence events of the same group of lines of response, a geometric factor value of each group of lines of response, where each line of response in the same group of lines of response has a same geometric factor value;
- cyclically calculating crystal efficiency factor values of the plurality of crystals; and
- calculating normalization factor values of the plurality of lines of response respectively, according to the geometric factor value and the crystal efficiency factor values.

According to some embodiments, the detector includes M crystal rings, each crystal ring includes N crystals; and the calculating a geometric symmetry value of each line of response includes: calculating the geometric symmetry value of each line of response according to:

$$gk_{u,v} = \left||n_u - n_v| - N/2\right|,$$

where $gk_{u,v}$ represents a geometric symmetry value of a line of response, u, v respectively represent serial numbers of crystal rings on which two crystals connected by a line of response are located, $0 \le u \le M-1$, $0 \le v \le M-1$, $n_u$ represents a crystal serial number of one of the two crystals connected by the line of response on a ring u, and $n_v$ represents a crystal serial number of the other one of the two crystals connected by the line of response on a ring v, $0 \le n_u \le N-1$, $0 \le n_v \le N-1$, N represents a total number of the crystals on each crystal ring, N is a positive even number, and M represents a total number of the crystal rings included in the detector, M is a natural number.

According to some embodiments, the normalization correction method further includes: before calculating the geometric symmetry value of each line of response, initializing the geometric factor value of each line of response among the plurality of lines of response, and initializing an efficiency factor value of each crystal.

According to some embodiments, the geometric factor of each group of lines of response and the crystal efficiency factor values of the plurality of crystals are cyclically calculated by using a maximum-likelihood estimation method.

According to some embodiments, cyclically calculating the geometric factor value of each group of lines of response includes: calculating a geometric factor value of a group of lines of response according to an equation, $$g_{u,v} = \frac{\sum_{ij} m_{ij}}{\sum_{ij} \varepsilon_i * \varepsilon_j * P_{ij}},$$

where $g_{u,v}$ represents a geometric factor value of lines of response having the same geometric symmetry value on the ring u and the ring v, $m_{ij}$ represents an actual number of coincidence events detected by a line of response formed by a crystal i and a crystal j, where i and j each represent a serial number of a crystal respectively, $\varepsilon_i$ represents a detection efficiency factor value of the crystal i, $\varepsilon_j$ represents a detection efficiency factor value of the crystal j, $P_{ij}$ represents a sum of probabilities of the line of response passing through each voxel.

According to some embodiments, the cyclically calculating crystal efficiency factor values of the plurality of crystals includes: calculating the crystal efficiency factor values of the plurality of crystals according to an equation, $$\varepsilon_i = \frac{\sum_j m_{ij}}{\sum_j \varepsilon_j * g_{ij} * P_{ij}},$$

where $g_{ij}$ represents the geometric factor value of the line of response formed by the crystal i and the crystal j.

According to some embodiments, the calculating normalization factor values of the plurality of lines of response respectively, according to the geometric factor value and the crystal efficiency factor value, includes: calculating a normalization factor value of each line of response according to an equation, $$\varphi_{ij} = \varepsilon_i * \varepsilon_j * g_{u,v},$$

where $\varphi_{ij}$ represents the normalization factor value of the line of response formed by the crystal i and the crystal j.

According to some embodiments, the calculating normalization factor values of the plurality of lines of response respectively, according to the geometric factor value and the crystal efficiency factor values, includes:

calculating a convergence value of the normalization factor value by successive iteration; and when a difference between convergence values of two adjacent iterations is less than a specified threshold, terminating the iterative calculating and determining a current normalization factor value as the normalization factor value of the line of response.

According to some embodiments, the calculating a convergence value of the normalization factor value by successive iteration includes: calculating the convergence value of the normalization factor value through an equation, $$s = \sqrt{\frac{\sum_{ij}\left(\frac{\varphi_{ij}}{\dot{\varphi}_{ij}} - 1\right)^2}{C}},$$

where $\dot{\varphi}_{ij}$ represents a normalization factor value of the line of response formed by the crystal i and the crystal j in a previous iteration, C represents a total number of lines of response, S represents the convergence value.

According to some embodiments, the specified threshold is about 0.0001.

According to some embodiments, the normalization correction method further includes: outputting a normalization factor distribution map in a three-dimensional data volume format.

In another aspect, a normalization correction apparatus for a PET system is provided, where the PET system includes a detector, the detector includes a plurality of crystals, and the normalization correction apparatus includes:

an acquisition module configured to acquire a coincidence event dataset, where the coincidence event dataset includes a plurality of lines of response;

a geometric symmetry value calculation module configured to calculate a geometric symmetry value of each line of response;

a grouping module configured to group the plurality of lines of response according to the geometric symmetry value of each line of response, where a plurality of lines of response in a group of lines of response have a same geometric symmetry value;

an accumulation module configured to calculate a number of coincidence events of a same group of lines of response through accumulation;

a geometric factor value calculation module configured to cyclically calculate a geometric factor value of each group of lines of response according to the calculated number of the coincidence events of the same group of lines of response, where each line of response in the same group of lines of response has a same geometric factor value;

a crystal efficiency factor value calculation module configured to cyclically calculate crystal efficiency factor values of the plurality of crystals; and a normalization factor value calculation module configured to calculate normalization factor values of the plurality of lines of response respectively, according to the geometric factor value and the crystal efficiency factor values.

In yet another aspect, an electronic device is provided, including:

one or more processors; and a storage device configured to store one or more programs, where the one or more programs, when executed by the one or more processors, cause the one or more processors to implement the normalization correction method described above.

In still another aspect, a computer readable storage medium storing executable instructions is provided, where the instructions, when executed by a processor, implement the normalization correction method described above.

BRIEF DESCRIPTION OF THE DRAWINGS

By referring to the accompanying drawings for a detailed description of exemplary embodiments of the present disclosure, features and advantages of the present disclosure will become more apparent.

DETAILED DESCRIPTION OF EMBODIMENTS

Figure 1A:
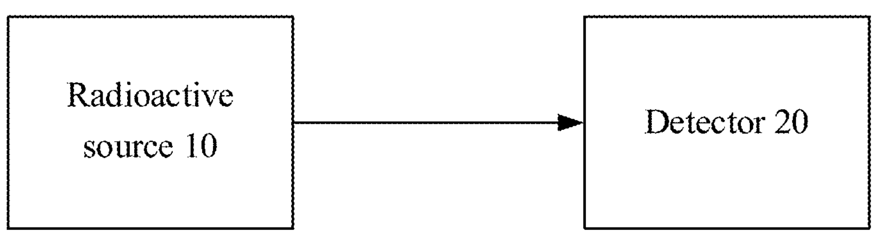
FIG. 1A is a schematic block diagram of a PET system.

In order to make the purpose, technical solution, and advantages of embodiments of the present disclosure clearer, the technical solution in the embodiments of the present disclosure will be described clearly and completely with reference to the accompanying drawings. Apparently, the embodiments described are only some embodiments of the present disclosure, rather than all embodiments. Based on the described embodiments of the present disclosure, all other embodiments derived by those of ordinary skill in the art without creative labor fall within the scope of protection of the present disclosure.

It should be noted that in the accompanying drawings, for purposes of clarity and/or description, a size and relative size of a component may be amplified. In this way, the size and relative size of each component do not have to be limited to the size and relative size shown in the figures. In the specification and accompanying drawings, the same or similar reference numeral indicates the same or similar part.

In order to facilitate description, spatial relationship terms such as "up", "down", "left", "right", etc. may be used here to describe a relationship between a component or feature and another component or feature as shown in the figures. It should be understood that the spatial relationship terms are intended to cover different orientations in which an apparatus is used or operated in addition to the orientation described in the figures. For example, if the apparatus in the figures is upside down, the component described as "under" or "below" other components or features will be oriented as "on" or "above" other components or features.

It should be noted that, in this article, the expression "PET" is an abbreviation of Positron Emission Tomography. In a PET system, a clinical imaging process specifically includes that a radioactive nuclide (such as F-18, etc.) which emits positrons is marked onto a compound that may participate in human tissue blood flow or metabolic process, and the radioactive nuclide of the compound marked with the positrons is injected into a body of the patient. A PET scanning is performed on the patient within an effective field of view (FOV) of the PET. The positrons emitted by the radioactive nuclide move about 1 mm in the body and combine with negatrons in the tissue to produce annihilation radiation, so as to generate two γ photons with equal energy (511 KeV) and opposite directions. By using a detection system of a PET apparatus, it is possible to detect the pair of γ photons, so as to analyze the presence of positrons and reconstruct a PET image that reflects a metabolism of various tissues of an organism, thereby obtaining a concentration distribution of a tracer in the body of the organism being detected.

A detection channel (hereinafter referred to as "channel") is the most basic unit for receiving γ photon signals. Each channel is coupled to only one crystal. Since paths of the two photons in the body are different, there is also a certain difference in the time they take to reach the two detection channels. If the detection system detects two photons that are 180 degrees (±0.25 degrees) from each other within a specified time window (usually 0-15 ns), it is called a "coincidence event". A "connecting line" between a pair of detectors that satisfy the "coincidence event" is called a projection line, or referred to as line of response (LOR for short). For any detection channel i, as shown in FIG. 1, there are a certain number of detection channels j in the detection system that may form a line of response with the $i^{th}$ detection channel.

In a process of PET imaging, due to factors such as geometric structure and hardware performance, the sensitivity of detectors at different positions in the detection system is often inconsistent, thereby causing data distortion and pseudo-shadow in a final image. The method used to eliminate sensitivity differences between detector channels is called a normalization correction method. The principle of traditional component-based PET normalization correction method is to correct according to a counting rate of each line of response. This method generally calculates the detection efficiency of each channel first, and then sequentially calculates geometric factors of the detector, axial position of a detection ring, and radial position of the detection ring, where each channel is located. Finally, the normalization factor of each line of response is obtained by multiplying the channel detection efficiencies at two ends of the line of response and the geometric factor.

In a process of forming a PET image for diagnosis (this process is referred to as image reconstruction), a system response matrix is used. The essence of the system response matrix is an array of probabilities that photons generated by each pixel in the image are detected by a certain line of response. The system response matrix is generally obtained through mathematical calculation, software simulation, and other methods, which may not be completely consistent with an actual detection system, thereby causing abnormal phenomena such as ring pseudo-shadow in the image. Therefore, in order to obtain a correct image, it is required to correct a sensitivity of the actual detection system to be consistent with a sensitivity of the system response matrix, and the normalization correction is a method used to correct the detection probability difference mentioned above.

The inventor discovered through research that an initial normalization correction method began in the 1980s. A spatially consistently distributed radioactive source is placed within an effective imaging field of view of the PET system, and then the number of events collected within each detection crystal range is obtained, that is a probe count. The normalization correction factor corresponding to each detection crystal is calculated through the probe count of each detection crystal. This method is called a direct normalization method. This method requires statistics of a large amount of data and takes a long time to collect. In 1989, Hoffman proposed a component-based normalization method. Compared with the direct normalization, the component-based normalization method takes into account a mutual influence between correction factors such as the crystal detection efficiency of the PET system and the geometric difference factor of the line of response. The component normalization is relatively complex to be implemented for 3D PET, and requires a large amount of coincidence event data to calculate a high-precision normalization factor. In addition, there are also some methods to obtain correction factors through iteration. However, the above methods need to calculate the normalization factor for each LOR. When the LOR collects no coincidence event data or detects insufficient coincidence event data, the calculated normalization factor will be inaccurate.

Embodiments of the present disclosure provide at least a normalization correction method for a PET system, where the PET system includes a detector, and the detector includes a plurality of crystals. The normalization correction method includes: acquiring a coincidence event dataset, where the coincidence event dataset includes a plurality of lines of response; calculating a geometric symmetry value of each line of response; grouping the plurality of lines of response according to the geometric symmetry value of each line of response, where a plurality of lines of response in a group of lines of response have a same geometric symmetry value; calculating a number of coincidence events of a same group of lines of response through accumulation; cyclically calculating, according to the calculated number of the coincidence events of the same group of lines of response, a geometric factor value of each group of lines of response, where each line of response in the same group of lines of response has a same geometric factor value; cyclically calculating crystal efficiency factor values of the plurality of crystals; and calculating normalization factor values of the plurality of lines of response respectively, according to the geometric factor value and the crystal efficiency factor values mentioned above. In the normalization correction method according to embodiments of the present disclosure, geometric symmetry is added to solve the geometric factor value, so that it is possible to calculate a high-precision normalization factor based on a small amount of data, which is beneficial to reducing the amount of calculation and improving calculation accuracy.

FIG. 1A is a schematic block diagram of a PET system. With reference to FIG. 1A, the PET system may include a radioactive source 10 and a detector 20. For example, a detector for the PET system may include components such as crystals, light guides, photomultiplier tubes, and preamplifier circuits.

Figure 1B:
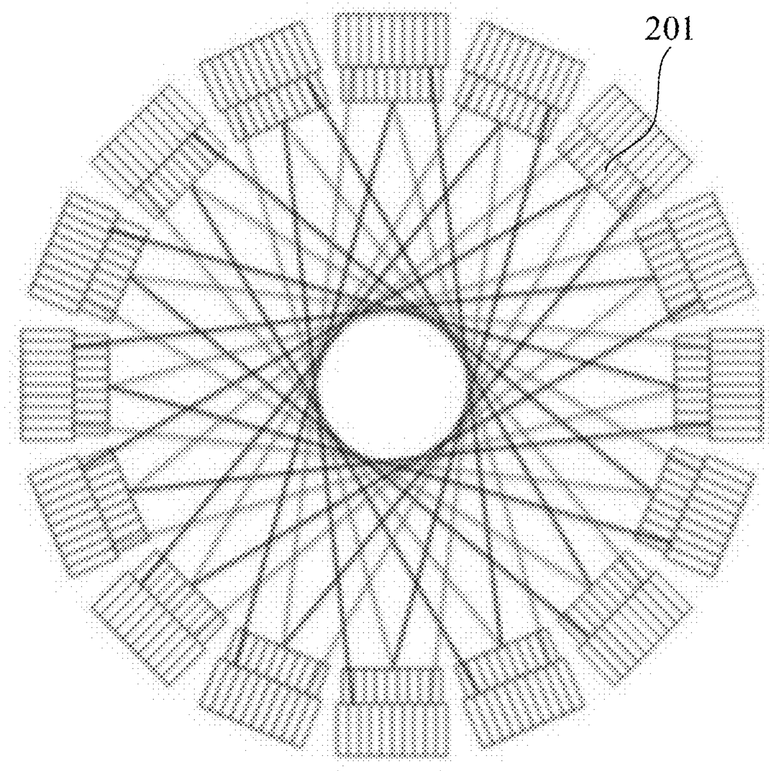
FIG. 1B is a cross-sectional schematic diagram of a detector of the PET system.

FIG. 1B is a cross-sectional schematic diagram of a detector of the PET system. With reference to FIG. 1B, the detector 20 may include a plurality of detection rings. Each detection ring may be assembled from a plurality of detector modules. For example, each detector module may include a scintillation crystal 201 and a photomultiplier tube. The scintillation crystal may absorb γ photons and generate a certain number of visible light photons according to the energy of γ photons. The photomultiplier tube may convert the visible light generated by the scintillation crystal into an electrical signal output, for example, into a pulse signal output.

It should be noted that in embodiments of the present disclosure, the detector 20 may include a plurality of crystal rings. Correspondingly, the PET system may be a 3D PET system.

Figure 2:
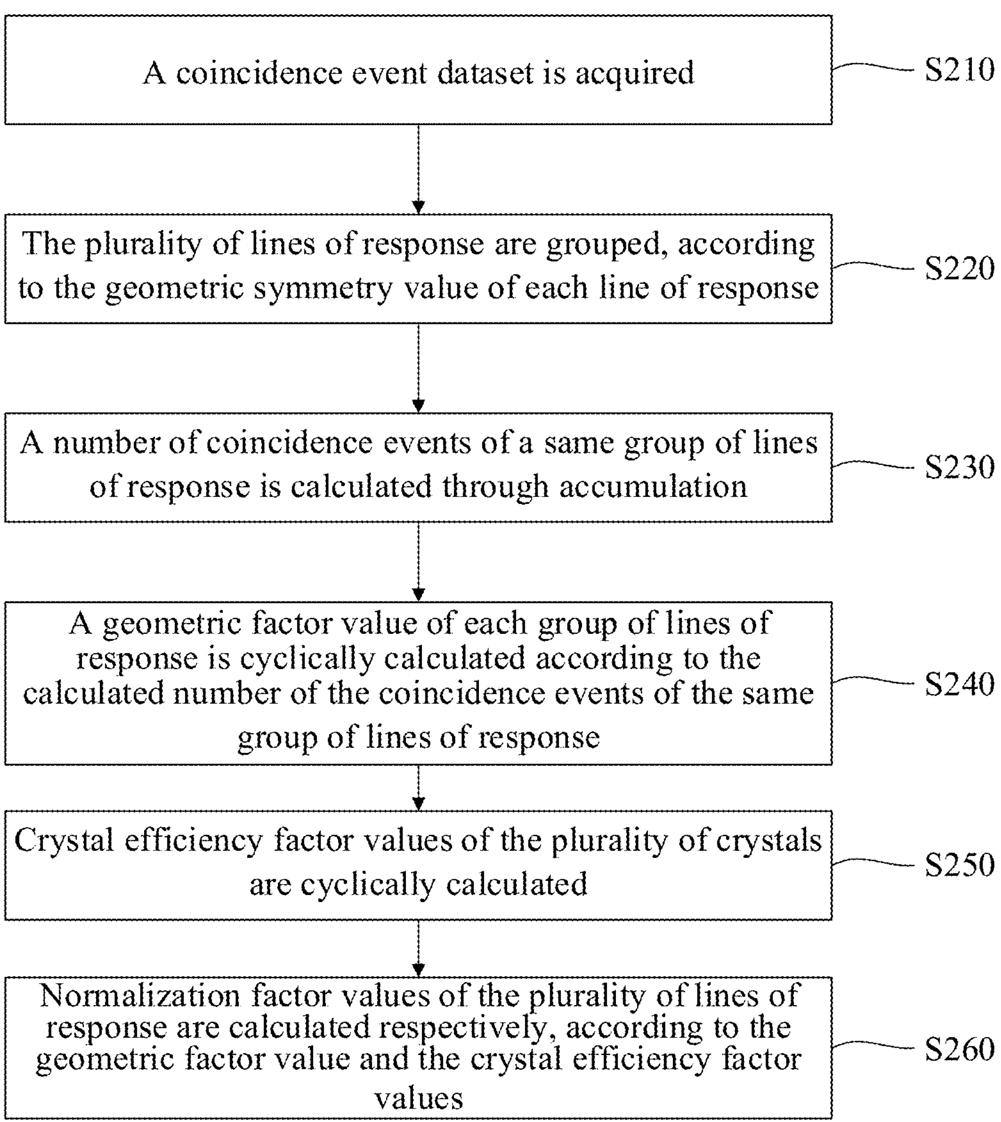
FIG. 2 is a flowchart of a normalization correction method for a PET system according to some exemplary embodiments of the present disclosure.

FIG. 2 is a flowchart of a normalization correction method for a PET system according to some exemplary embodiments of the present disclosure. With reference to FIG. 1, a normalization correction method 200 for the PET system may include operations and steps as follows.

In operation S210, a coincidence event dataset is acquired, where the coincidence event dataset includes a plurality of lines of response; and a geometric symmetry value of each line of response is calculated.

In operation S220, the plurality of lines of response are grouped according to the geometric symmetry value of each line of response, where a plurality of lines of response in a group of lines of response have a same geometric symmetry value.

In operation S230, a number of coincidence events of a same group of lines of response is calculated through accumulation.

In operation S240, a geometric factor value of each group of lines of response is cyclically calculated according to the calculated number of the coincidence events of the same group of lines of response, where each line of response in the same group of lines of response has a same geometric factor value.

In operation S250, crystal efficiency factor values of the plurality of crystals are cyclically calculated.

In operation S260, normalization factor values of the plurality of lines of response are calculated respectively, according to the geometric factor value and the crystal efficiency factor values.

Figure 3:
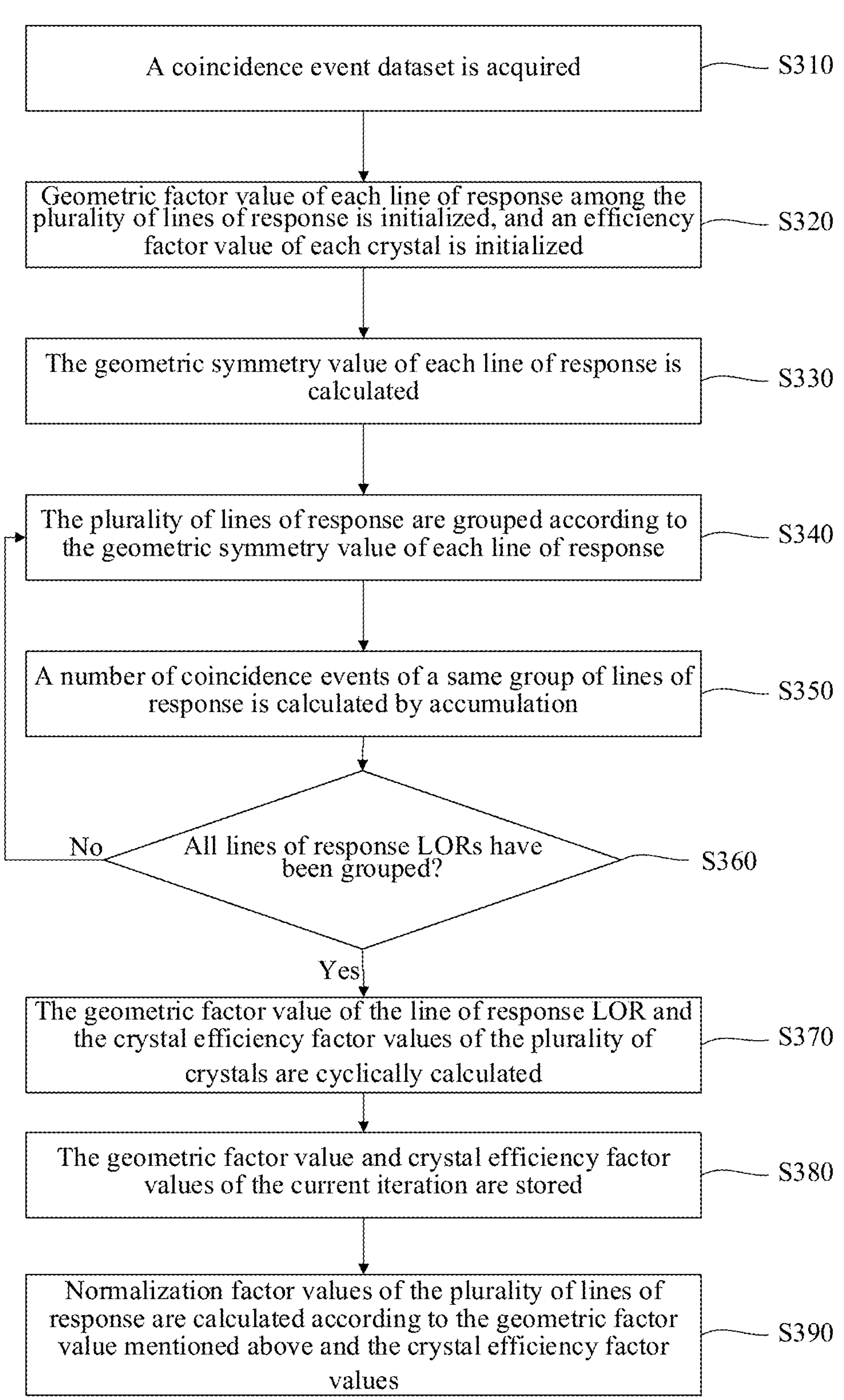
FIG. 3 is a detailed flowchart of a normalization correction method for a PET system according to some exemplary embodiments of the present disclosure.

FIG. 3 is a detailed flowchart of a normalization correction method for a PET system according to some exemplary embodiments of the present disclosure. With reference to FIG. 2 and FIG. 3, the normalization correction method 200 for the PET system may include operations and steps as follows.

In operation S310, a coincidence event dataset is acquired. For example, coincidence events may be collected through a brain PET system. Specifically, FDG (abbreviated as fluorodeoxyglucose) is injected using a ring prosthesis to collect data.

It should be noted that in this embodiment, the normalization correction method is explained using the brain PET system as an example. However, embodiments of the present disclosure are not limited to the brain PET system.

In operation S320, geometric factor value of each line of response among the plurality of lines of response is initialized, and an efficiency factor value of each crystal is initialized. For example, an initial value of the geometric factor value of each line of response may be 1, and an initial value of the efficiency factor value of each crystal may be 1.

In operation S330, the geometric symmetry value of each line of response is calculated.

For example, the detector 20 may include M crystal rings, and each crystal ring includes N crystals.

The calculating a geometric symmetry value of each line of response may include: calculating the geometric symmetry value of each line of response according to an equation (1), $$gk_{u,v} = \left| |n_u - n_v| - N/2 \right|, \quad \text{equation (1)}$$

where $gk_{u,v}$ represents a geometric symmetry value of a line of response, u and v respectively represent serial numbers of crystal rings on which two crystals connected by a line of response are located, $0 \le u \le M-1$, $0 \le v \le M-1$, $n_u$ represents a crystal serial number of one of the two crystals connected by the line of response on a ring u, and $n_v$ represents a crystal serial number of the other one of the two crystals connected by the line of response on a ring v, $\theta \le n_u \le N-1$, $\theta \le n_v \le N-1$ N represents a total number of the crystals on each crystal ring, N is a positive even number, and M represents a total number of the crystal rings included in the detector, M is a natural number.

In operation S340, the plurality of lines of response are grouped according to the geometric symmetry value of each line of response, where a plurality of lines of response in a group of lines of response have a same geometric symmetry value.

For example, with reference to FIG. 1B, a plurality of lines of response LORs having the same geometric symmetry value are schematically shown. The geometric symmetry value of each line of response LOR is calculated according to the equation (1), and the lines of response LORs having the same geometric symmetry value are divided into one group, so as to obtain a plurality of groups of lines of response LORs. In each group of lines of response LORs, the geometric symmetry value of each line of response LOR is the same.

In operation S350, a number of coincidence events of a same group of lines of response is calculated by accumulation. That is, the number of coincidence events is accumulated for the same group of lines of response by: $\Sigma_{ij} m_{ij}$, where i=0, . . . , N−1 and j=0, . . . , N−1. Corresponding crystals at two ends of the line of response LOR are crystal i and crystal j, respectively, and "$m_{ij}$" is an actual number of coincidence events detected by the line of response LOR formed by the crystal i and the crystal j.

Specifically, there is symmetry in the lines of response LORs on the crystal ring (referred to as a structure formed by a plurality of crystals arranged in a shape of ring), and it may be considered that lines of response LORs with the same symmetry have a same geometric position, that is, the geometric factor values are the same.

In operation S360, it is determined whether or not all lines of response LORs have been grouped. If the grouping operation is not completed, it will be returned to perform the above operation S340. If the grouping operation is completed, the following steps will be performed.

In operation S370, the geometric factor value of the lines of response LORs and the crystal efficiency factor values of the plurality of crystals are cyclically calculated.

In embodiments of the present disclosure, a normalization model is defined to describe the number of coincidence events detected by each line of response LOR as follows:

$$M_{ij} = \varepsilon_i * \varepsilon_j * g_{ij} * P_{ij} * A_{ij}, \quad \text{equation (2)}$$

where corresponding crystals at two ends of the line of response LOR are crystal i and crystal j; $M_{ij}$ represents a number of coincidence events detected by the line of response LOR in an ideal state; $\varepsilon_i$ represents a detection efficiency factor value of the crystal i, and $\varepsilon_j$ represents a detection efficiency factor value of the crystal j; $g_{ij}$ represents the geometric factor value of the line of response LOR formed by the crystal i and the crystal j; $P_{ij}$ represents a sum of probabilities of the line of response LOR formed by the crystal i and the crystal j passing through each voxel, the value of $P_{ij}$ may be obtained from a system response matrix; and $A_{ij}$ represents a concentration value of the radioactive source.

The calculation of equation (2) needs to find the values of $g_{ij}$, $\varepsilon_i$ and $\varepsilon_j$, but there are many unknown variables in the above equation and it may not be solved directly. In embodiments of the present disclosure, the normalization factor value may be solved based on a maximum-likelihood estimation method.

For example, a likelihood function NL may be established as follows:

$$NL = \sum_{ij} [m_{ij} * \log(M_{ij}) - M_{ij}]. \quad \text{equation (3)}$$

It is required to maximize the likelihood function NL, take a logarithm, find a first derivative, and obtain a factor when the first derivative is zero. By combining the equations (2) and (3), the following equations may be obtained:

$$\varepsilon_i = \frac{\sum_j m_{ij}}{\sum_j \varepsilon_j * g_{ij} * P_{ij}}, \quad \text{equation (4)}$$

$$g_{ij} = \frac{m_{ij}}{\varepsilon_i * \varepsilon_j * P_{ij}}. \quad \text{equation (5)}$$

Through continuous iterative operations based on the equations (4) and (5), all crystal efficiency factor values and geometric factor values of the lines of response LORs may be calculated. In embodiments of the present disclosure, a symmetry geometric relationship of the LORs in a three-dimensional space is calculated, the LORs having the same geometric symmetry relationship are classified into one same group, and LORs in the group have the same geometric factor value. In this way, a high-precision normalization factor value may be calculated based on a small amount of data.

In embodiments of the present disclosure, each line of response in the same group of lines of response has the same geometric factor value.

For example, cyclically calculating the geometric factor value of each group of lines of response includes: calculating a geometric factor value of a group of lines of response according to an equation (6) as follows, $$g_{u,v} = \frac{\sum_{ij} m_{ij}}{\sum_{ij} \varepsilon_i * \varepsilon_j * P_{ij}}, \quad \text{equation (6)}$$

where $g_{u,v}$ represents a geometric factor value of lines of response having the same geometric symmetry value on the ring u and the ring v, my represents an actual number of coincidence events detected by a line of response formed by a crystal i and a crystal j, where i and j each represent a serial number of a crystal respectively, $\varepsilon_i$ represents a detection efficiency factor value of the crystal i, $\varepsilon_j$ represents a detection efficiency factor value of the crystal j, and $P_{ij}$ represents a sum of probabilities of the line of response passing through each crystal.

For example, according to the above equation (4), the crystal efficiency factor values of all crystals may be cyclically calculated.

In operation S380, the geometric factor value and crystal efficiency factor values of the current iteration are stored.

In operation S390, normalization factor values of the plurality of lines of response are calculated according to the geometric factor value mentioned above and the crystal efficiency factor values.

For example, the normalization factor values of all lines of response LORs may be calculated according to an equation (7) as follows:

$$\varphi_{ij} = \varepsilon_i * \varepsilon_j * g_{u,v}, \quad \text{equation (7)}$$

where $\varphi_{ij}$ represents the normalization factor value of the line of response formed by the crystal i and the crystal j.

In operation S410, a convergence value of the normalization factor value is calculated by successive iteration; and when a difference between convergence values of two adjacent iterations is less than a specified threshold, the iterative calculating is terminated and a current normalization factor value is determined as the normalization factor value of the line of response.

For example, the calculating a convergence value of the normalization factor value by successive iteration may include: calculating the convergence value of the normalization factor value through an equation (8) as follows, $$S = \sqrt{\frac{\sum_{ij}\left(\frac{\varphi'_{ij}}{\varphi_{ij}} - 1\right)^2}{C}}, \quad \text{equation (8)}$$

where $\dot{\varphi}_{ij}$ represents a normalization factor value of the line of response formed by the crystal i and the crystal j in a previous iteration, C represents a total number of lines of response, and S represents the convergence value.

For example, the specified threshold is about 0.0001. Specifically, the difference Δd between the convergence values of two adjacent iterations is calculated according to an equation (9):

$$\Delta d = |S_C - S_P|, \quad \text{equation (9)}$$

when Δd is greater than 0.0001, the above S370 is performed; and when Δd is less than 0.0001, the following operations or steps are performed.

Optionally, in operation S420, a normalization factor value is output to an MLEM reconstruction algorithm, where a probability value of the line of response LOR passing through the voxel is set to 1.

Figure 4A:
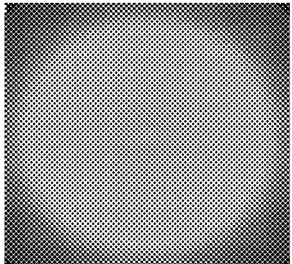
FIG. 4A to FIG. 4C are slices of three-dimensional data volume with normalization factors according to some exemplary embodiments of the present disclosure, respectively.
Figure 4B:
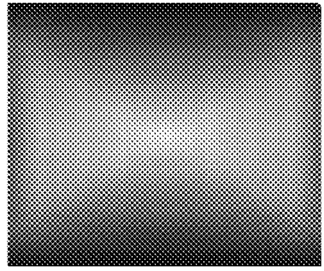
Figure 4C:
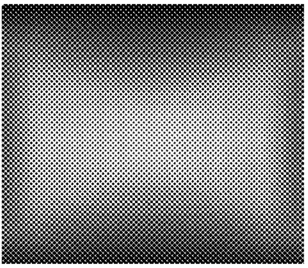

In operation S430, a normalization factor distribution map in a three-dimensional data volume format is output. FIG. 4A to FIG. 4C are slices of three-dimensional data volume with normalization factors according to some exemplary embodiments of the present disclosure, respectively. With reference to FIG. 4A to FIG. 4C, it may be seen that the distribution of normalization factors is consistent with the distribution of pseudo-shadow in a normally reconstructed image, so that it is possible to determine that the distribution trend of normalization factors is correct.

Figure 5:
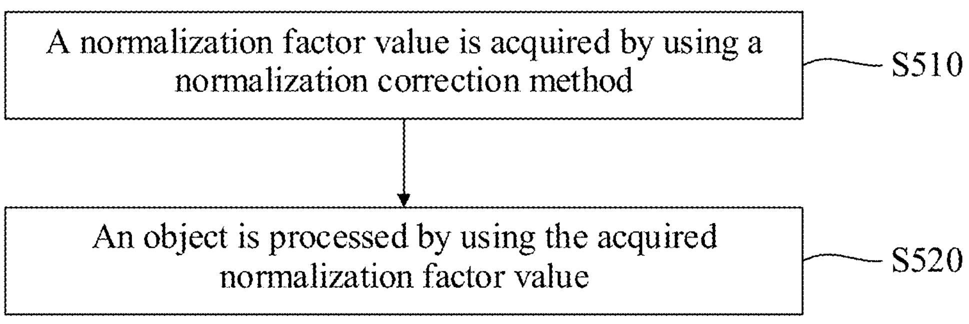
FIG. 5 is a flowchart of a method of processing an image according to some exemplary embodiments of the present disclosure.

According to embodiments of the present disclosure, a method of processing an image is also provided. With reference to FIG. 5, the method of processing the image includes operations or steps as follows.

In operation S510, a normalization factor value is acquired by using the normalization correction method described above.

In operation S520, an object is processed by using the acquired normalization factor value.

For example, a same ROI is intercepted from an image that uses the normalization factor value and an image that does not use the normalization factor value, and a uniformity is quantitatively calculate, so as to obtain the following data sheet.

| Image | Mean value | Standard deviation | Uniformity (%) |
|---|---|---|---|
| normalization used | 0.083 | 0.002 | 2.4 |
| No normalization used | 0.099 | 0.004 | 4.0 |

From the above sheet, it may be seen that in the image using the normalization factor values, the standard deviation is smaller. In the above data sheet, the uniformity is equal to the standard deviation divided by the mean value. The smaller the value of the uniformity, the better the uniformity of the image. It may be seen that the uniformity of the image is greatly improved by using the normalization factor value to process the image.

Figure 6:
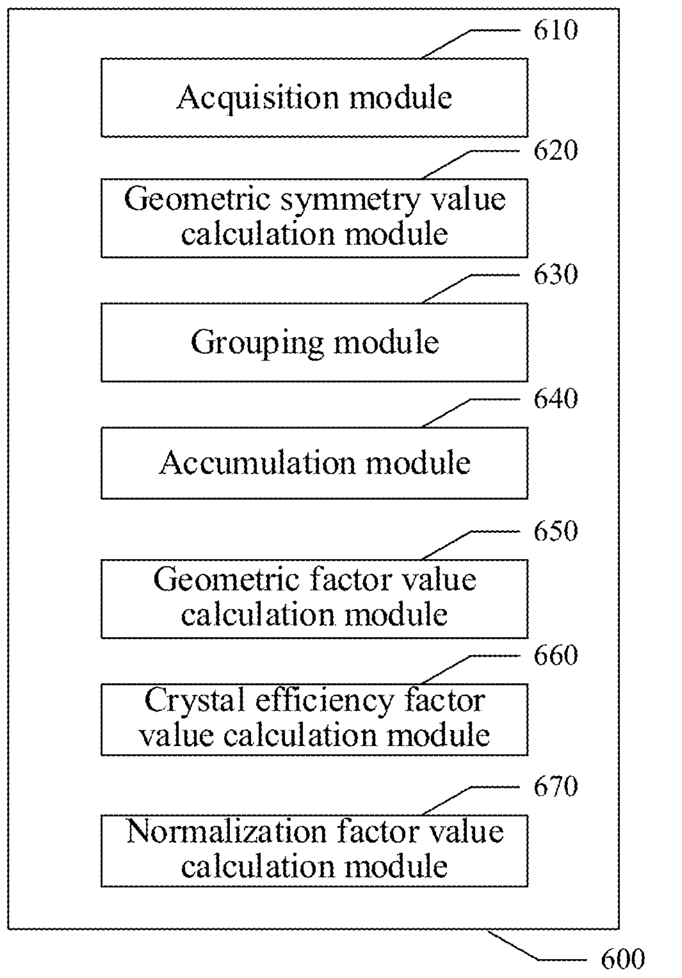
FIG. 6 is a schematic block diagram of a normalization correction apparatus for a PET system according to some exemplary embodiments of the present disclosure.

FIG. 6 is a schematic block diagram of a normalization correction apparatus for a PET system according to some exemplary embodiments of the present disclosure. With reference to FIG. 6, the PET system includes a detector, and the detector includes a plurality of crystals. The normalization correction apparatus 600 may include: an acquisition module 610 used to acquire a coincidence event dataset, where the coincidence event dataset includes a plurality of lines of response; a geometric symmetry value calculation module 620 used to calculate a geometric symmetry value of each line of response; a grouping module 630 used to group the plurality of lines of response according to the geometric symmetry value of each line of response, where a plurality of lines of response in a group of lines of response have a same geometric symmetry value; an accumulation module 640 used to calculate a number of coincidence events of a same group of lines of response through accumulation; a geometric factor value calculation module 650 used to cyclically calculate a geometric factor value of each group of lines of response according to the calculated number of the coincidence events of the same group of lines of response, where each line of response in the same group of lines of response has a same geometric factor value; a crystal efficiency factor value calculation module 660 used to cyclically calculate crystal efficiency factor values of the plurality of crystals; and a normalization factor value calculation module 670 used to calculate normalization factor values of the plurality of lines of response respectively, according to the geometric factor value and the crystal efficiency factor values mentioned above.

According to embodiments of the present disclosure, any two or more modules and units in the normalization correction apparatus may be combined and implemented into one module, or any one module may be split into a plurality of modules. Alternatively, at least some of functions of one or more of these modules may be combined with at least some of the functions of other modules and implemented in one module. According to embodiments of the present disclosure, at least one of the modules and units in the above-mentioned normalization correction apparatus may be at least partially implemented as a hardware circuit, such as a field programmable gate array (FPGA), a programmable logic array (PLA), an on-a-chip system, a system on a substrate, a system on encapsulation, and an application specific integrated circuit (ASIC). Alternatively, it may be implemented by hardware or firmware through any other reasonable means of integrating or encapsulating circuits, or through any one of three implementation methods of software, hardware and firmware, or an appropriate combination of any of them. Alternatively, at least one of the modules and units in the normalization correction apparatus mentioned above may be at least partially implemented as a computer program module, and when the computer program module is executed, corresponding functions may be performed.

In the normalization correction method and normalization correction apparatus according to embodiments of the present disclosure, the normalization factor may be accurately calculated, and the portability is strong. In the iteration process, the method of adding geometric symmetry of the line of response LOR may calculate geometric factors based on a small amount of data. In addition, a normalization factor visualization method for the 3D PET systems is also provided to facilitate analysis and verification of the correctness of normalization factors.

Figure 7:
FIG. 7 schematically shows a block diagram of an electronic device suitable for implementing a normalization correction method mentioned above according to embodiments of the present disclosure.
Figure 7:
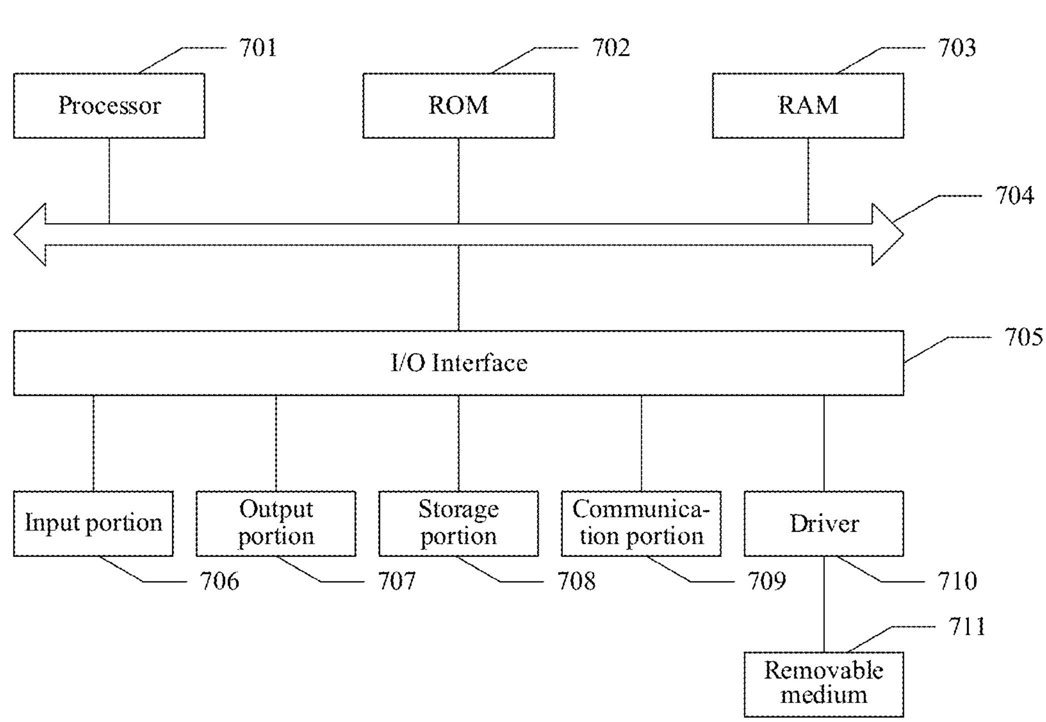

FIG. 7 schematically shows a block diagram of an electronic device suitable for implementing a normalization correction method according to embodiments of the present disclosure.

As shown in FIG. 7, the electronic apparatus 700 according to embodiments of the present disclosure includes a processor 701, which may perform various appropriate actions and processes according to programs stored in a read-only memory (ROM) 702 or programs loaded from a storage portion 708 into a random access memory (RAM) 703. The processor 701 may include, for example, a general-purpose microprocessor (such as CPU), an instruction set processor and/or a related chipset, and/or a specialized microprocessor (such as application specific integrated circuit (ASIC)), and so on. The processor 701 may also include an onboard memory for caching purposes. The processor 701 may include a single processing unit or a plurality of processing units for performing different actions of the method flow according to embodiments of the present disclosure.

In the RAM 703, various programs and data required for operations of an electronic device 700 are stored. The processor 701, ROM 702 and RAM 703 are connected to each other through a bus 704. The processor 701 performs various operations of the method flow according to embodiments of the present disclosure by performing programs in ROM 702 and/or RAM 703. It should be noted that the program may also be stored in one or more storage devices other than ROM 702 and RAM 703. The processor 701 may also perform various operations of the method flow according to embodiments of the present disclosure by performing programs stored in the one or more storage device.

According to embodiments of the present disclosure, the electronic device 700 may further include an input/output (I/O) interface 705. The input/output (I/O) interface 705 is also connected to the bus 704. The electronic device 700 may also include one or more of the following components connected to the I/O interface 705; an input portion 706 including a keyboard, a mouse, etc; an output portion 707 including a cathode ray tube (CRT), a liquid crystal display (LCD) and a speaker; a storage portion 708 including a hard disk, etc; and a communication portion 709 including a network interface card such as LAN card, a modem, etc. The communication portion 709 performs communication processing through a network such as the Internet. A driver 710 is also connected to the I/O interface 705 as desired. A removable medium 711, such as a disk, an optical disk, a magneto-optical disk, a semiconductor memory, etc., are mounted on the driver 710 as desired, so as to facilitate mounting computer programs read from the driver 710 into the storage portion 708 as desired.

The present disclosure also provides a computer-readable storage medium. The computer-readable storage medium may be included in the device/apparatus/system described in the above embodiments. It may also exist separately without being assembled into the device/apparatus/system. The computer-readable storage medium mentioned above stores one or more programs, where the one or more programs, when executed, implement the method according to embodiments of the present disclosure.

According to embodiments of the present disclosure, the computer-readable storage medium may be a non-volatile computer-readable storage medium, such as but not limited to: a portable computer disk, a hard disk, a random access memory (RAM), a read-only memory (ROM), an erasable programmable read-only memory (EPROM or flash memory), a portable compact disk read-only memory (CD-ROM), an optical storage devices, a magnetic storage device or any suitable combination of the above. In the present disclosure, the computer-readable storage medium may be any tangible medium that contains or stores a program, which may be used by or in combination with an instruction execution system, an apparatus or a device. For example, according to embodiments of the present disclosure, the computer-readable storage medium may include one or more storage devices other than ROM 702 and/or RAM 703, and/or ROM 702 and RAM 703 as described above.

Embodiments of the present disclosure further include a computer program product, which includes a computer program containing program code for executing the method shown in the flowchart. When the computer program product is running in the computer system, the program code is used to cause the computer system to implement an item recommendation method provided in embodiments of the present disclosure.

When the computer program is executed by the processor 701, the above-mentioned functions defined in the system/apparatus of embodiments of the present disclosure are executed. According to embodiments of the present disclosure, the systems, apparatuses, modules, units, etc. described above may be implemented through computer program modules.

In an embodiment, the computer program may rely on tangible storage medium such as an optical storage device and a magnetic memory device. In another embodiment, the computer program may also be transmitted, distributed in the form of signals on the network medium, and downloaded and installed through the communication portion 709, and/or installed from the removable medium 711. The program code contained in this computer program may be transmitted using any suitable network medium, including but not limited to: wireless, wired, etc., or any suitable combination of the above.

In such embodiments, the computer program may be downloaded and installed from the network through the communication portion 709, and/or installed from the removable medium 711. When the computer program is executed by the processor 701, the above-mentioned functions defined in the system of embodiments of the present disclosure are executed. According to embodiments of the present disclosure, the systems, devices, apparatuses, modules, units, etc. described above may be implemented through computer program modules.

According to embodiments of the present disclosure, the program code for executing the computer program provided by embodiments of the present disclosure may be written in any combination of one or more programming languages. Specifically, these computing programs may be implemented using advanced procedures and/or object-oriented programming languages, and/or assembly/machine languages. Programming languages include but are not limited to programming languages such as Java, C++, Python, "C" language or similar programming languages. The program code may be completely executed on user computing devices, partially executed on user devices, partially executed on remote computing devices, or completely executed on remote computing devices or servers. In a case of involving remote computing devices, the remote computing devices may be connected to user computing devices through any type of networks, including a local area network (LAN) or a wide area network (WAN), or may be connected to external computing devices (such as using an Internet service provider to be connected through the Internet).

The flowcharts and block diagrams in the figures illustrate the architecture, functionality, and operations of possible implementations of systems, methods, and computer program products according to various embodiments of the present disclosure. In this regard, each block in the flowcharts or block diagrams may represent a module, program segment, or part of codes that contains one or more logic functions that implement the specified executable instructions. It should also be noted that, in some alternative implementations, the functions noted in the block may also occur in a different order than those indicated in the figures. For example, two blocks shown one after another may actually execute substantially in parallel, or they may also be executed in the reverse order, depending on the functionality involved. It should also be noted that each block in the block diagram or flowchart, and the combination of blocks in the block diagrams or flowcharts, may be implemented by using dedicated hardware-based systems that perform specified functions or operations, or may be implemented by using a combination of dedicated hardware and computer instructions.

Those skilled in the art may understand that the features described in various embodiments and/or claims of the present disclosure may be combined or conjunctive in various ways, even if such combinations or conjunctions are not explicitly described in the present disclosure. In particular, without departing from the spirit and teachings of the present disclosure, the features described in various embodiments and/or claims of the present disclosure may be combined and/or conjunctive in various ways. All such combinations and/or conjunctions fall within the scope of the present disclosure.

Embodiments of the present disclosure have been described above. However, these embodiments are for illustrative purposes only and are not intended to limit the scope of the present disclosure. Although each embodiment is described separately above, this does not mean that the measures in the various embodiments may not be used in conjunction to advantage. The scope of the present disclosure is limited by the accompanying claims and their equivalents. Without departing from the scope of the present disclosure, those skilled in the art may make various substitutions and modifications, all of which should fall within the scope of the present disclosure.

What is claimed is:

1. A normalization correction method for a PET system, wherein the PET system comprises a detector, the detector comprises a plurality of crystals, and the normalization correction method comprises:

acquiring a coincidence event dataset, wherein the coincidence event dataset comprises a plurality of lines of response;

calculating a geometric symmetry value of each line of response;

grouping the plurality of lines of response according to the geometric symmetry value of each line of response, wherein a plurality of lines of response in a group of lines of response have a same geometric symmetry value;

calculating a number of coincidence events of a same group of lines of response through accumulation;

cyclically calculating, according to the calculated number of the coincidence events of the same group of lines of response, a geometric factor value of each group of lines of response, wherein each line of response in the same group of lines of response has a same geometric factor value;

cyclically calculating crystal efficiency factor values of the plurality of crystals; and calculating normalization factor values of the plurality of lines of response respectively, according to the geometric factor value and the crystal efficiency factor values;

wherein the detector comprises M crystal rings, each crystal ring comprises N crystals; and the calculating a geometric symmetry value of each line of response comprises:

calculating the geometric symmetry value of each line of response according to:

$$gk_{u,v} = \left| |n_u - n_v| - N/2 \right|,$$

where $gk_{u,v}$ represents a geometric symmetry value of a line of response, u, v respectively represent serial numbers of crystal rings on which two crystals connected by a line of response are located, $0 \le u \le M-1$, $0 \le v \le M-1$, $n_u$ represents a crystal serial number of one of the two crystals connected by the line of response on a ring u, and $n_v$ represents a crystal serial number of the other one of the two crystals connected by the line of response on a ring v, $0 \le n_u \le N-1$, $0 \le n_v \le N-1$, N represents a total number of the crystals on each crystal ring, N is a positive even number, and M represents a total number of the crystal rings comprised in the detector, M is a natural number.

2. The normalization correction method of claim 1, further comprising: before calculating the geometric symmetry value of each line of response, initializing the geometric factor value of each line of response among the plurality of lines of response, and initializing an efficiency factor value of each crystal.

3. The normalization correction method of claim 1, comprising:

cyclically calculating the geometric factor value of each group of lines of response and the crystal efficiency factor values of the plurality of crystals by using a maximum-likelihood estimation method.

4. The normalization correction method of claim 1, wherein cyclically calculating the geometric factor value of each group of lines of response comprises: calculating a geometric factor value of a group of lines of response according to:

$$g_{u,v} = \frac{\sum_{ij} m_{ij}}{\sum_{ij} \varepsilon_i * \varepsilon_j * P_{ij}},$$

where $g_{u,v}$ represents a geometric factor value of lines of response having the same geometric symmetry value on the ring u and the ring v, $m_{ij}$ represents an actual number of coincidence events detected by a line of response formed by a crystal i and a crystal j, where i and j each represent a serial number of a crystal respectively, $\varepsilon_i$ represents a detection efficiency factor value of the crystal i, $\varepsilon_j$ represents a detection efficiency factor value of the crystal j, $P_{ij}$ represents a sum of probabilities of the line of response passing through each voxel.

5. The normalization correction method of claim 4, wherein the cyclically calculating crystal efficiency factor values of the plurality of crystals comprises: calculating the crystal efficiency factor values of the plurality of crystals according to:

$$\varepsilon_i = \frac{\sum_j m_{ij}}{\sum_j \varepsilon_j * g_{ij} * P_{ij}},$$

where $g_{ij}$ represents the geometric factor value of the line of response formed by the crystal i and the crystal j.

6. The normalization correction method of claim 5, wherein the calculating normalization factor values of the plurality of lines of response respectively, according to the geometric factor value and the crystal efficiency factor values, comprises: calculating a normalization factor value of each line of response according to:

$$\varphi_{ij} = \varepsilon_i * \varepsilon_j * g_{u,v},$$

where $\varphi_{ij}$ represents the normalization factor value of the line of response formed by the crystal i and the crystal j.

7. The normalization correction method of claim 6, wherein the calculating normalization factor values of the plurality of lines of response respectively, according to the geometric factor value and the crystal efficiency factor values, comprises:

calculating a convergence value of the normalization factor value by successive iteration; and when a difference between convergence values of two adjacent iterations is less than a specified threshold, terminating the iterative calculating and determining a current normalization factor value as the normalization factor value of the line of response.

8. The normalization correction method of claim 7, wherein the calculating a convergence value of the normalization factor value by successive iteration comprises: calculating the convergence value of the normalization factor value through:

$$S = \sqrt{\frac{\sum_{ij}\left(\frac{\varphi'_{ij}}{\varphi_{ij}} - 1\right)^2}{C}},$$

where $\varphi_{ij}$ represents a normalization factor value of the line of response formed by the crystal i and the crystal j in a previous iteration, C represents a total number of lines of response, S represents the convergence value.

9. The normalization correction method of claim 7, wherein the specified threshold is about 0.0001.

10. The normalization correction method of claim 1, further comprising:

outputting a normalization factor distribution map in a three-dimensional data volume format.

11. An electronic device, comprising:

one or more processors; and a storage device configured to store one or more programs, wherein the one or more programs, when executed by the one or more processors, cause the one or more processors to implement the normalization correction method of any one of claim 1.

12. The electronic device of claim 11, wherein before calculating the geometric symmetry value of each line of response, the one or more processors are further configured for:

initializing the geometric factor value of each line of response among the plurality of lines of response, and initializing an efficiency factor value of each crystal.

13. The electronic device of claim 11, wherein the one or more processors are further configured for:

cyclically calculating the geometric factor of each group of lines of response and the crystal efficiency factor values of the plurality of crystals by using a maximum-likelihood estimation method.

14. The electronic device of claim 11, wherein the one or more processors are further configured for: calculating a geometric factor value of a group of lines of response according to:

$$g_{u,v} = \frac{\sum_{ij} m_{ij}}{\sum_{ij} \varepsilon_i * \varepsilon_j * P_{ij}},$$

where $g_{u,v}$ represents a geometric factor value of lines of response having the same geometric symmetry value on the ring u and the ring v, $m_{ij}$ represents an actual number of coincidence events detected by a line of response formed by a crystal i and a crystal j, where i and j each represent a serial number of a crystal respectively, $\varepsilon_i$ represents a detection efficiency factor value of the crystal i, $\varepsilon_j$ represents a detection efficiency factor value of the crystal j, $P_{ij}$ represents a sum of probabilities of the line of response passing through each voxel.

15. The electronic device of claim 14, wherein the one or more processors are further configured for: calculating the crystal efficiency factor values of the plurality of crystals according to:

$$\varepsilon_i = \frac{\sum_j m_{ij}}{\sum_j \varepsilon_j * g_j * P_{ij}},$$

where $g_{ij}$ represents the geometric factor value of the line of response formed by the crystal i and the crystal j.

16. The electronic device of claim 15, wherein the one or more processors are further configured for: calculating a normalization factor value of each line of response according to:

$$\varphi_{ij} = \varepsilon_i * \varepsilon_j * g_{u,v},$$

where $\varphi_{ij}$ represents the normalization factor value of the line of response formed by the crystal i and the crystal j.

17. The electronic device of claim 16, wherein the one or more processors are further configured for:

calculating a convergence value of the normalization factor value by successive iteration; and when a difference between convergence values of two adjacent iterations is less than a specified threshold, terminating the iterative calculating and determining a current normalization factor value as the normalization factor value of the line of response.

18. A non-transitory computer-readable storage medium storing executable instructions, wherein the instructions, when executed by a processor, implement the normalization correction method of any one of claim 1.

* * * * *